United States Patent [19]

Shampanier

[11] Patent Number: 5,564,925
[45] Date of Patent: Oct. 15, 1996

[54] IMPLANT FOR AN ARTIFICIAL TOOTH

[76] Inventor: Avi Shampanier, No. 5, Moriah Ave., Haifa, Israel, 34751

[21] Appl. No.: 427,157

[22] Filed: Apr. 24, 1995

[30] Foreign Application Priority Data

Mar. 14, 1995 [IL] Israel ......................................... 112989

[51] Int. Cl.$^6$ .................................................. A61C 8/00
[52] U.S. Cl. ...................................................... 433/173
[58] Field of Search ................................. 433/172, 173, 433/174, 175, 176

[56] References Cited

U.S. PATENT DOCUMENTS

| 3,474,537 | 10/1969 | Christensen | 433/174 |
| 3,808,606 | 5/1974 | Tronzo | 433/173 X |
| 5,133,662 | 7/1992 | Metcalfe | 433/172 X |
| 5,201,736 | 4/1993 | Strauss | 433/173 X |
| 5,246,370 | 9/1993 | Coatoam | 433/173 |

FOREIGN PATENT DOCUMENTS 2681777 4/1993 France ................................. 433/172

Primary Examiner—Nicholas D. Lucchesi
Attorney, Agent, or Firm—Frishauf, Holtz, Goodman, Langer & Chick

[57] ABSTRACT

An implant for an artificial tooth suitable for insertion into a jaw portion of low height includes a circular dish-shaped outer portion having a concave surface towards the tooth to be attached and a convex surface adjoining a concave surface provided in the bone surface, and a short anchor pin extending from the center of the convex surface of the dish for insertion into a drilled bore in the bone. A tapped bore extends from the center of the dish into the anchor pin and permits firm mounting of an abutment to the implant by a screw inside a cavity in the abutment. The abutment has a concave bottom surface which permits its attachment to the implant at a certain angle. The dish-shaped portion includes four bores arranged around its center serving for firm attachment of the implant to the bone by four small screws.

13 Claims, 2 Drawing Sheets

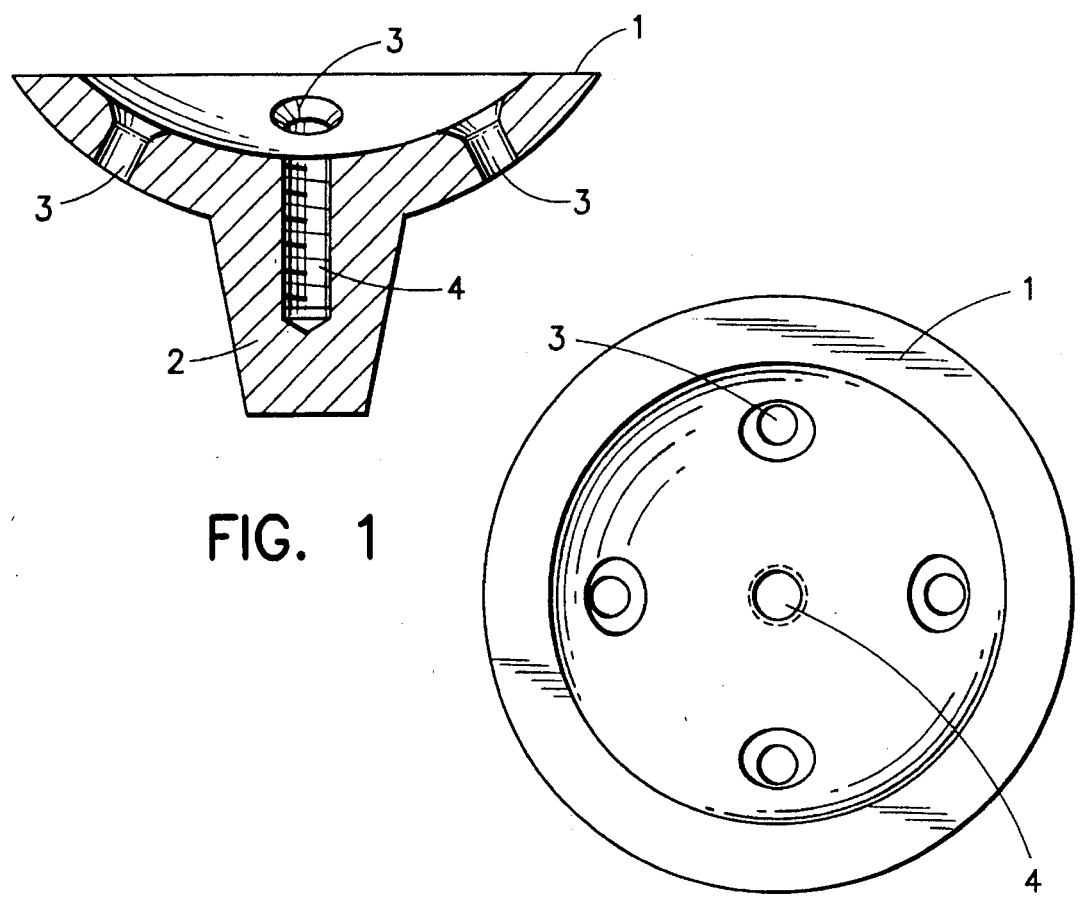
FIG. 1
FIG. 2
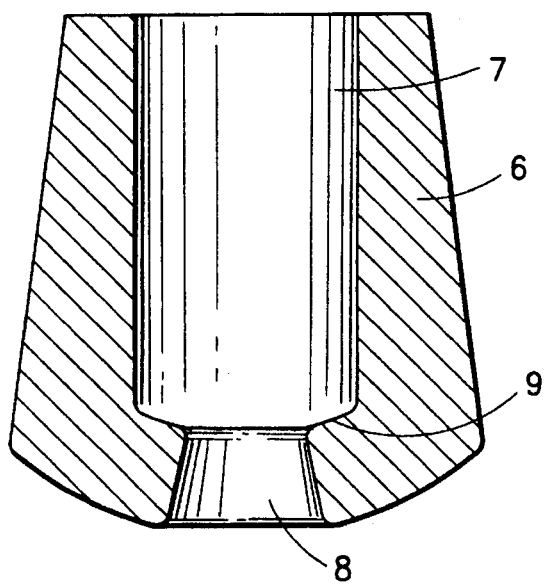
FIG. 3

IMPLANT FOR AN ARTIFICIAL TOOTH

The invention relates to an implant for an artificial tooth, particularly to an implant for fixing an artificial tooth replacement in a jaw of low bone height or of limited space due to anatomical structure.

BACKGROUND OF THE INVENTION

Edentate or partly edentate persons tend more and more to have their removable dentures replaced by firmly implanted teeth, either single or in the form of multiple tooth bridges, a fact that has led to the design of various shapes and kinds of implants to which a crown can be firmly and permanently attached.

The conventional and commonly used implant includes a fixture of Titanium provided with external and internal screw threads to be placed into the jaw bone.

The main drawback of these pin-shaped and threaded implants is the requirement of their being of sufficient length in order to support the tooth against forces caused by chewing and biting; this necessary length limits their insertion mainly into the frontal, incisor portion of the jaws, while the jaw bone along the lateral sides is in many cases too low for accommodating the long implants. In addition, the sinus cavities in the upper half of the skull are usually too close for providing sufficient bone depth for long implants of the above kind. Another obstacle is the mandibular nerve in the lower jaw, likewise limiting the depth or angulation to which the implant can penetrate. Still another disadvantage of the conventional implant is that the bore for insertion of the fixture has to be drilled more or less parallel to the outer contours of the jaw bone, whereby the direction of the axes of implant and tooth diverge to a large degree, and make rehabilitation a difficult task.

With the aim to overcoming the drawback of the long screw implant, various implants of shorter depth have been developed configured to enter the bone to a relatively low depth.

It is therefore the main object of the present invention to provide an implant designed for implanting artificial teeth in jaw portions regardless of low height, otherwise unsuitable for tooth restoration by means of conventional implants.

It is another object to provide an implant and an abutment configured to be attached to the implant at an angle not coaxial with the implant with the aim to fastening the crown in correct angular alignment.

Another object of the invention is to provide an implant that can withstand lateral forces in a more favorable manner than with the conventional implants.

Still another object is to remove from the jaw a minimum of bone material.

SUMMARY OF THE INVENTION

In order to better define the different components of the implant and abutment it will be understood that in the following the term "inner" shall indicate the direction towards the inside of the jaw, and the term "outer" shall indicate the direction towards the artificial tooth to be fastened.

According to the present invention an implant consists of a material compatible with bone and tissue of the jaw, such as Titanium, but other suitable materials may be discovered in the future to be used for manufacture of the different components.

The implant includes an outer dish-shaped portion, having an outer, concave surface preferably in the form of a spherical section, the dish being perforated by at least two—but preferably four—bores configured to accommodate one screw each for fastening the dish to the bone surface. A short pin-shaped anchor extends in inner direction from the center of the dish and contains a coaxial tapped bore penetrating the center of the dish. The anchor pin is preferably in the form of a cone frustum with its inner end of smaller diameter, for facilitating its insertion in a bore in the jaw.

The invention includes an abutment to be firmly fastened to the implant and having the crown or artificial tooth firmly attached onto it. The abutment is a frustum of a cone or a pyramid having an inner end of convex shape with its radius corresponding to that of the concave portion of the dish, a hollow concentric portion open at the outer end and continued at its inner end by a conical bore of increasing diameter towards the inner end.

Connection of the abutment to the implant is by means of a screw fitting into the tapped bore of the implant and extending through the conical bore of the abutment into the tapped bore thereby permitting the abutment to be mounted with its axis either in coaxial or in angular alignment in relation to the implant axis.

BRIEF DESCRIPTION OF THE DRAWINGS

FIG. 1, is a cross section of the dish-shaped implant body.

FIG. 2, is a top view of the implant body of FIG. 1,

FIG. 3, is a longitudinal section of an abutment,

DETAILED DESCRIPTION OF THE DRAWINGS

Figure 4:
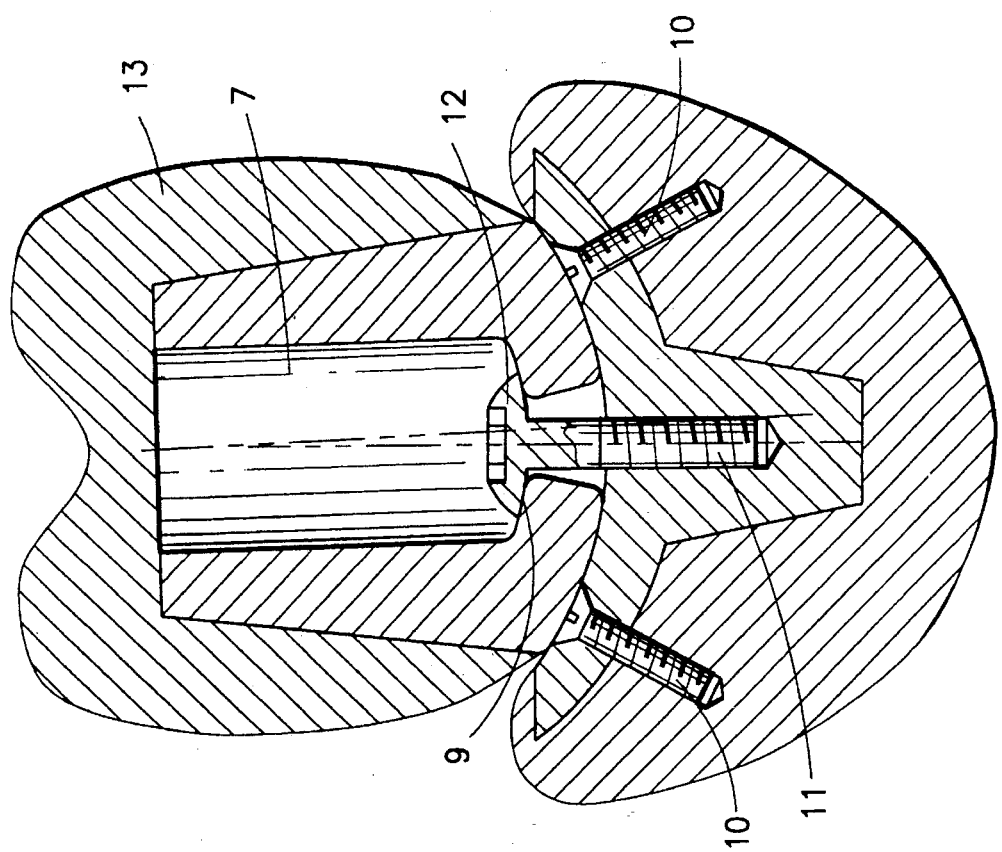
FIG. 4, is an assembly of implant, abutment and crown implanted in a jaw.

The implant body shown in FIGS. 1 and 2 includes an outer dish-shaped portion 1 and an anchor pin 2 in concentric alignment. The dish is perforated by four countersunk holes 3 arranged around its center, while a tapped bore 4 is concentric with the dish and anchor pin stopping short off the inner end of the pin. The pin 2 is slightly decreasing in diameter towards its inner end in order to facilitate its insertion into a predrilled bore in the bone. The outer dish surface 5 is in the form of a spherical section to permit correct positioning of the abutment of similar configuration.

FIG. 3 shows an embodiment of an abutment suitable for fixation to the implant in the form of a cone frustum 6 of a cross section decreasing towards the outer end and having an inner, convex end of a spherical configuration co-extensive with that of the outer concave surface of the dish-shaped portion. It contains a central cavity 7 open at the outer end and terminating in a concave bottom end 9 short of the inner end of the frustum. A bore 8 extends from the end 9 to the outside in coaxial alignment with the cavity and with its cross section increasing towards the inner end of the abutment. The abutment may be similarly formed in the shape of a pyramidal frustom.

Figure 5:
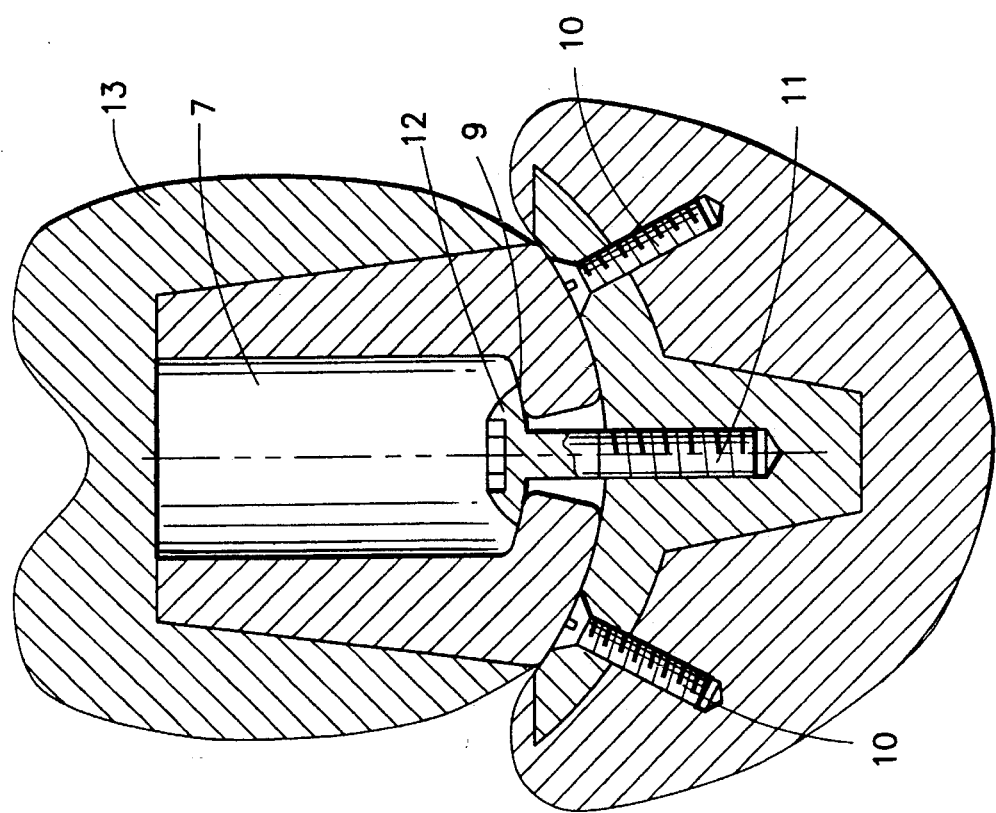
FIG. 5, shows an assembly similar to that illustrated in FIG. 4, with the abutment axis forming an angle with the axis of the implant.

FIG. 4 and 5 show the assembly of the different components implanted into a jaw, with an artificial tooth crown 13 affixed to the abutment. The FIGURES show fastening of the implant to the jaw by means of at least two screws 10 and firm connection between implant and abutment by a central screwed bolt 11. In FIG. 4 implant and abutment are shown to be in coaxial alignment, and in FIG. 5 in angular alignment, respectively. The bolt 11 is shown to have its head 12 rounded on the side contacting the concave bottom end 9 of cavity 7 in order to permit angular positioning of the abutment on the implant.

The operation is similar to that while using a conventional implant, but with the difference that less bone material has to be removed for accommodation of the implant.

The foregoing description refers to the mounting of a single artificial tooth on the implant, but in dental practice it is the custom to provide a small number of spaced-apart implants along the upper or lower jaw and affix to these a bridge containing several or even all necessary teeth. The implant of the present invention is most suitable for the latter task, since its low height permits its provision in the molar section, a matter practically impossible with long implants.

Reiterating the advantages of the present implant and abutment, it can be said that:

It permits variability of restorations with minimal components and minimal trouble-shooting.

It permits the implantologist to place the implants where they are needed for rehabilitation regardless of local limitations.

The implant and abutment are designed to withstand lateral forces in a compensational way.

It obviates the need of precise parallelization at the surgical phase.

It is suitable for single and multiple unit restorations.

It provides maximum support for restoration materials with minimum danger of fractures.

The osseous support of the implant can be enhanced at a later stage, by placement of a failing screw without sacrificing the entire implant.

I claim:

1. A dental implant for fastening an artificial tooth or a bridge containing at least one artificial tooth to the bone of an upper or a lower jaw, said dental implant comprising:
   an implant body adapted to be firmly implanted in the jaw bone; and
   an abutment adapted to be rigidly fastened to said implant body;
   said implant body having an outer end and an inner end adapted to extend into the jaw bone, and said implant body comprising:
   a dish-shaped portion having an outer concave surface and a convex surface adapted to be attached to a pre-shaped recess in the jaw bone of a shape conforming to said outer convex surface of said dish-shaped portion, said dish-shaped portion being perforated by at least two bores distanced from a center of said dish-shaped portion;
   an anchor pin of circular cross section integral with said dish-shaped portion and extending from the center of said outer convex surface of said dish-shaped portion for anchoring said implant body in a prepared bore in the jaw bone;
   a screw-threaded bore extending centrally through said dish-shaped portion into said anchor pin; and
   at least two screws adapted to extend through said at least two bores into the jaw bone effecting firm connection of said implant body to said jaw.

2. The dental implant of claim 1, wherein said dish-shaped portion of said implant body is perforated by four bores for fastening said implant body to the jaw bone by four screws.

3. The dental implant of claim 1, wherein said outer concave surface of said dish-shaped portion of said implant body is in the form of a spherical section.

4. The dental implant of claim 1, wherein said screw-threaded bore of said implant body stops short of an inner end of said anchor pin of said implant body.

5. The dental implant of claim 1, wherein said abutment is in the shape of a frustum having an inner end adapted to be connected to said implant body and an outer end of a smaller cross section than said inner end, said inner end having a convex shape conforming to the outer concave surface of said dish-shaped portion of said implant body, said abutment being centrally perforated by a cavity open at the outer end of said abutment, said cavity having an inner bottom end distanced from the inner convex end of said abutment, and said inner end of said abutment having a bore extending therethrough in communication with said cavity, said bore having a smaller diameter than said cavity and a cross section which increases from said cavity to said inner end of said abutment.

6. The dental implant of claim 5, wherein said abutment is in the shape of a conical frustum.

7. The dental implant of claim 5, wherein said inner bottom end of said cavity in said abutment has a concave shape.

8. The dental implant of claim 5, further comprising a screw for fastening said abutment to said implant body, said screw including a head abutting on said inner bottom end of said cavity in said abutment and said screw having an inner end provided with a screw-thread corresponding to said screw-threaded bore in said implant body.

9. The dental implant of claim 8, wherein said inner bottom end of said cavity in said abutment has a concave shape and said head of said screw has an inner surface rounded corresponding to said concave-shaped inner bottom end of said cavity to permit said abutment to be fastened to said implant body in angular alignment.

10. The dental implant of claim 5, wherein said bore in said inner end of said abutment is coaxially aligned with said cavity in said abutment.

11. The dental implant of claim 1, wherein an axis of said abutment and an axis of said implant body are coincident.

12. The dental implant of claim 1, wherein an axis of said abutment and an axis of said implant body are not coincident.

13. The dental implant of claim 1 wherein said dish-shaped portion of said implant body has a circular shape.

* * * * *